US012781337B2

(12) United States Patent
Dacus et al.

(10) Patent No.: US 12,781,337 B2
(45) Date of Patent: *Nov. 3, 2026

(54) ORTHOPEDIC IMPLANTS HAVING A SUBSURFACE LEVEL CERAMIC LAYER APPLIED VIA BOMBARDMENT

(71) Applicant: Joint Development, LLC, Salt Lake City, UT (US)

(72) Inventors: Eric M. Dacus, Salt Lake City, UT (US); Erin E. Hofmann, Park City, UT (US); Dermott J. McHugh, Salt Lake City, UT (US)

(73) Assignee: Joint Development, Inc., Salt Lake City, UT (US)

( * ) Notice: Subject to any disclaimer, the term of this patent is extended or adjusted under 35 U.S.C. 154(b) by 1134 days.

This patent is subject to a terminal disclaimer.

(21) Appl. No.: 17/713,771

(22) Filed: Apr. 5, 2022

(65) Prior Publication Data

US 2022/0228258 A1 Jul. 21, 2022

Related U.S. Application Data

(60) Continuation-in-part of application No. 16/680,248, filed on Nov. 11, 2019, now Pat. No. 12,416,077, (Continued)

(51) Int. Cl.
*C23C 16/24* (2006.01)
*A61F 2/30* (2006.01)
(Continued)

(52) U.S. Cl.
CPC ................ *C23C 16/24* (2013.01); *A61F 2/30* (2013.01); *A61L 27/34* (2013.01); (Continued)

(58) Field of Classification Search
CPC ...... A61F 2/30; A61F 2/32; A61F 2/34; A61F 2/36; A61F 2/38; A61F 2/40; A61F 2/42; (Continued)

(56) References Cited

U.S. PATENT DOCUMENTS

| | | | | |
|---|---|---|---|---|
| 5,520,664 A * | 5/1996 | Bricault, Jr. | ............ | A61L 29/16 604/174 |
| 6,280,844 B1 * | 8/2001 | Vesnovsky | ............ | C23C 14/022 428/615 |

(Continued)

*Primary Examiner* — Javier G Blanco

(74) *Attorney, Agent, or Firm* — Lowry Blixseth APC; Scott M. Lowry

(57) ABSTRACT

An orthopedic implant having a subsurface level ceramic layer generally includes a base material, an intermix layer molecularly integrated with the base material that includes a mixture of the base material and a plurality of subsurface level ceramic-based molecules implanted into the base material, and an integrated ceramic surface layer molecularly integrated with and extending from the intermix layer forming at least part of a molecular structure of an outer surface of the orthopedic implant. The integrated ceramic surface layer and the base material thereafter cooperate to sandwich the intermix layer in between.

18 Claims, 6 Drawing Sheets

Related U.S. Application Data which is a division of application No. 15/670,534, filed on Aug. 7, 2017, now Pat. No. 10,563,302.

(60) Provisional application No. 62/371,673, filed on Aug. 5, 2016.

(51) Int. Cl.

| | |
|---|---|
| ***A61L 27/34*** | (2006.01) |
| ***C23C 14/58*** | (2006.01) |
| ***C23C 16/34*** | (2006.01) |
| ***C23C 16/48*** | (2006.01) |
| *C23C 14/02* | (2006.01) |
| *C23C 14/06* | (2006.01) |
| *C23C 14/22* | (2006.01) |

(52) U.S. Cl.

CPC ........ *C23C 14/5833* (2013.01); *C23C 16/345* (2013.01); *C23C 16/486* (2013.01); *A61F 2002/30003* (2013.01); *A61F 2002/3006* (2013.01); *A61F 2002/30971* (2013.01); *A61F 2240/001* (2013.01); *A61F 2310/00317* (2013.01); *A61F 2310/00874* (2013.01); *C23C 14/024* (2013.01); *C23C 14/0652* (2013.01); *C23C 14/221* (2013.01)

(58) Field of Classification Search

CPC .................... A61F 2/44; A61F 2/30767; A61F 2002/30934; A61F 2002/30978; A61F 2002/3098; A61F 2002/30981; A61F 2002/30983; A61F 2310/00592; A61F 2310/00874; A61L 27/306; C23C 14/46; C23C 14/48; C23C 14/505; C23C 14/221

See application file for complete search history.

(56) References Cited

U.S. PATENT DOCUMENTS

| | | | | |
|---|---|---|---|---|
| 2005/0152089 | A1* | 7/2005 | Matsuda ................ | H02N 13/00 361/234 |
| 2006/0233944 | A1* | 10/2006 | Popoola .............. | C23C 14/5853 427/2.24 |
| 2008/0221683 | A1* | 9/2008 | Deutchman ........... | C23C 14/081 623/16.11 |
| 2017/0157289 | A1* | 6/2017 | Burns ................... | A61L 31/088 |

* cited by examiner

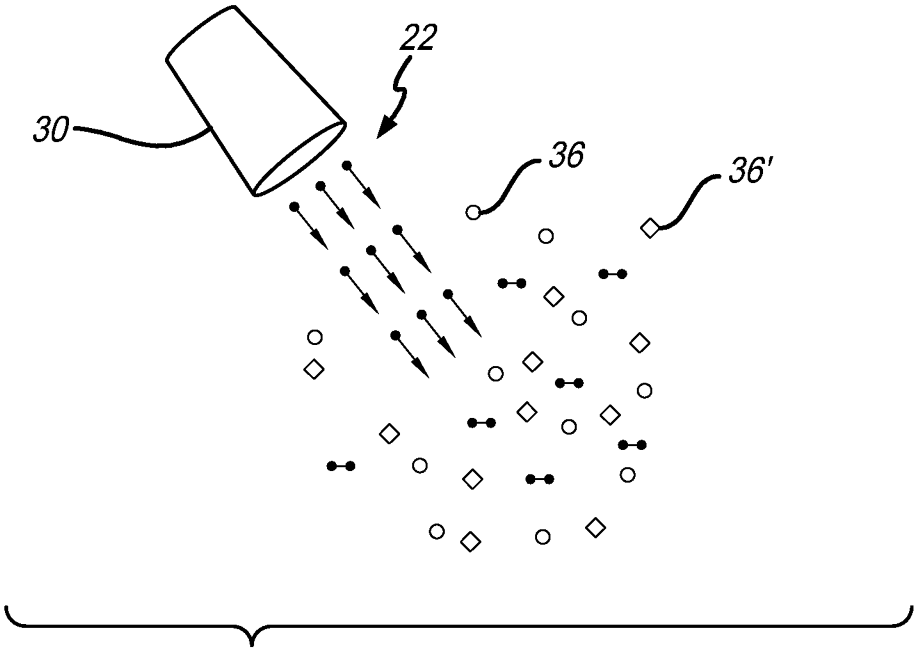
FIG. 3A
FIG. 3B
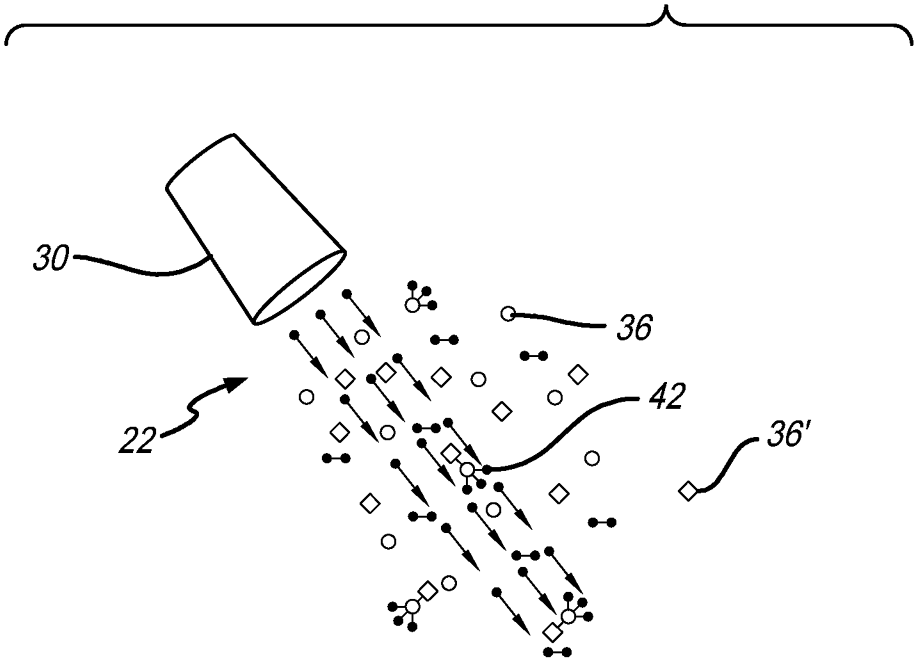

ORTHOPEDIC IMPLANTS HAVING A SUBSURFACE LEVEL CERAMIC LAYER APPLIED VIA BOMBARDMENT

BACKGROUND OF THE INVENTION

The present invention generally relates to orthopedic implants (e.g., hip, knee, shoulder replacements, etc.) having a subsurface level ceramic layer applied via ion bombardment, such as by way of an ion beam that causes molecular collisions that form a relatively uniform layer of ceramic molecules embedded in a subsurface of a target orthopedic implant.

Orthopedic implants (e.g., prosthetic joints to replace damaged hips, knees, shoulders, etc.) are commonly made of metal alloys such as cobalt chromium (CoCr) or titanium (Ti-6Al-4V). The mechanical properties of such metal alloys are particularly desirable for use in load-bearing applications, such as orthopedic implants. Although, when orthopedic implants are placed within the body, the physiological environment can cause the implant material to wear and corrode over time (especially articulatory surfaces), sometimes resulting in complications that require revision surgery. While hip and knee replacement surgery has been reported to be successful at reducing joint pain for 90-95% of patients, there are several complications that remain and the potential for revision surgery increases at a rate around 1% per year following a successful surgery. These complications can include infection and inflammatory tissue responses stemming from tribological debris particles from metal alloy implants, such as cobalt chromium, as a result of wear and corrosion over time.

To reduce the risk of complications from orthopedic implants, ceramic coatings have been applied to address the coefficient of friction of a wear couple, to specifically improve the surface roughness, and to reduce adhesion of a broad range of bacteria for purposes of reducing the rate of infection. For example, alumina ($Al_2O_3$) and zirconia ($ZrO_2$) are ceramics that have been used to coat the surfaces of orthopedic implants. These ceramic materials provide high wear resistance, reduced surface roughness, and high biocompatibility. But, both materials are not optimal for the fatigue loading of non-spherical geometry of most orthopedic implants due to poor tensile strength and low toughness. Accordingly, the disadvantages of these ceramic coatings, while addressing issues related to high wear resistance and surface roughness, cannot address other failure modes such as tensile strength and impact stresses.

Conventionally, ceramic coatings such as silicon nitride have been applied to the implant surface by a chemical vapor deposition (CVD) process or a physical vapor deposition (PVD) process. In one example, a PVD process is used to coat an implant joint with an external layer of silicon nitride. More specifically, such a process includes placing the implant, a silicon-containing material, and nitrogen gas ($N_2$) in a chamber that is heated to between 100-600 degrees Celsius. In response to the high temperatures, silicon atoms sputter from the silicon-containing material and subsequently react with the nitrogen gas at the heated surface of the implant to deposit a silicon nitride over-coat. One problem with this process is that there is no diffusion of the deposited silicon nitride molecules into the substrate material. That is, the silicon nitride is simply applied as an over-surface coating having a distinct boundary line between the deposited over-coating and the underlying substrate of the orthopedic implant. The adverse result is that the silicon nitride still experiences relatively poor surface adhesion and, over time, this over-surface coating can wear off, especially when the surface is an articulating surface (e.g., a ball-and-socket joint).

While vapor deposition of silicon nitride has been shown to work as an over-surface coating to certain orthopedic materials, such application is typically more expensive and less efficient than alumina or zirconia ceramic coatings. Moreover, it is often difficult, if not impossible, to attain a uniform application of silicon nitride to all surfaces of the orthopedic implant using known vapor deposition processes, such as those mentioned above. As a result, some areas of the over-surface coating have an undesirably thin layer of silicon nitride, wherein such areas are even more prone to reduced protection and wear. Alternatively, silicon nitride has also been used as the bulk or base material for orthopedic implants, but the production of a silicon nitride-based orthopedic implant is limited in size and inefficient to produce.

Recently, newer coating processes have been developed to provide greater adhesion by promoting diffusion of the coating material at the interface of the substrate and coating layers. Ion beam enhanced deposition (IBED), also known as ion beam assisted deposition (IBAD), is a process by which accelerated ions drive a vapor phase coating material into the subsurface of a substrate. Coatings applied by IBED may have greater adhesion than similar coatings applied by a conventional PVD process. Coatings applied by IBED may also have less delamination under impact stresses. For example, U.S. Pat. No. 7,790,216 to Popoola, the contents of which are herein incorporated by reference in their entirety, discloses a method of bombarding a medical implant with zirconium ions and then heating the implant in an oxygenated environment to induce the formation of zirconia ($ZrO_2$) at the surface. In this respect, the ion beam drives the zirconium ions to a certain depth within the surface of the implant known as the "intermix zone". Heat treatment within the oxygenated environment results in an embedded zirconia surface layer of approximately 5 micrometer (μm) thickness. The zirconia surface layer effectively penetrates the substrate and thereby resists delamination. But, this production method can be inefficient due to the high energy requirement for the heat treatment step. Likewise, the mechanical properties of the zirconia surface layer formed are not as desirable as those of a ceramic surface layer, which is incompatible with a heat treatment step.

There exists, therefore, a need in the art for orthopedic implants having a subsurface ceramic layer applied via ion bombardment that provides greater integration of ceramics into the implant, thereby providing greater resistance to the emission of tribological debris. The present invention fulfills these needs and provides further related advantages.

SUMMARY OF THE INVENTION

In one embodiment, an orthopedic implant as disclosed herein may include a base material, an intermix layer molecularly integrated with the base material that includes a mixture of the base material and a plurality of subsurface level ceramic-based molecules implanted into the base material, and an integrated ceramic surface layer molecularly integrated with and extending from the intermix layer and forming at least part of a molecular structure of an outer surface of the orthopedic implant. Here, the integrated ceramic surface layer and the base material may include an alloy bond therebetween at an atomic level formed by ion bombardment, and cooperate to sandwich the intermix layer in between. Once formed, the intermix layer may have a thickness of about 0.1-100 nanometers, and the combination of the intermix layer and the integrated ceramic surface layer may have an aggregate thickness of about 1-10,000 nanometers. As such, the orthopedic implant incorporating the integrated ceramic surface layer may thus have an electrical resistivity of about $10^{16}$ Ω·cm.

In another aspect of these embodiments, the integrated ceramic surface layer may be applied in a manner having a relatively uniform depth around the orthopedic implant, which may include a hip implant, a knee implant, or a shoulder implant. In some embodiments, the integrated ceramic surface layer may cover less than an entire surface area of the base material, such as on an articulating surface only. The ceramic-based molecules may include at least two different metalloid or transition metal atoms, such as metalloid atoms that include silicon atoms and transition metal atoms that include titanium, silver, gold, niobium, chromium, or molybdenum atoms. Moreover, the base material may be a metal alloy selected from the group consisting of cobalt, titanium, and zirconium, a ceramic material selected from the group consisting of alumina ($Al_2O_3$) and zirconia ($ZrO_2$), an organic polymer, or a composite organic polymer. Furthermore, the integrated ceramic surface layer may be selected from the group consisting of SiNAg, SiAuN, SiNbN, SiCrN, SiMoN, TiSiN, TiNAg, TiNAu, TiNbN, TiCrN, TiMoN, AgAuN, NbNAg, CrNAg, MoNAg AuNbN, AuCrN, AuMoN, NbCrN, NbMoN, or CrMoN.

In another embodiment, an orthopedic implant (e.g., a hip implant, a knee implant, or a shoulder implant) as disclosed herein may include a base material, an intermix layer molecularly integrated with the base material and having a thickness of about 0.1-100 nanometers, the intermix layer including a mixture of the base material and a plurality of subsurface level ceramic-based molecules implanted into the base material, and an integrated ceramic surface layer molecularly integrated with and extending from the intermix layer having a relatively uniform thickness forming at least part of the molecular structure of an articulating surface of the orthopedic implant. Here, the integrated ceramic surface layer and the base material may cooperate to sandwich the intermix layer in between, wherein the intermix layer and the integrated ceramic surface layer may have an aggregate thickness of about 1-10,000 nanometers. An alloy bond may be formed between the ceramic surface layer and the base material at an atomic level by ion bombardment.

Additionally, the ceramic-based molecules may be at least two different metalloid or transition metal atoms, wherein the metalloid atoms may be silicon and the transition metal atoms may be one of titanium, silver, gold, niobium, chromium, or molybdenum. In one embodiment, the integrated ceramic surface layer may cover less than an entire surface area of the base material, and the orthopedic implant incorporating the integrated ceramic surface layer may have an electrical resistivity of about $10^{16}$ Ω·cm. In another embodiment, the base material may be a metal alloy selected from the group consisting of cobalt, titanium, and zirconium, a ceramic material selected from the group consisting of alumina ($Al_2O_3$) and zirconia ($ZrO_2$), an organic polymer, or a composite organic polymer and the integrated ceramic surface layer may be selected from the group consisting of SiNAg, SiAuN, SiNbN, SiCrN, SiMoN, TiSiN, TiNAg, TiNAu, TiNbN, TiCrN, TiMoN, AgAuN, NbNAg, CrNAg, MoNAg AuNbN, AuCrN, AuMoN, NbCrN, NbMoN, or CrMoN.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 3*a* is a diagrammatic view illustrating interaction of an ion beam with vaporized metalloid and/or transition metal atoms;

FIG. 3*b* is a diagrammatic view illustrating the ion beam promoting reaction of the vaporized metalloid and/or transition metal atoms to form ceramic molecules;

DETAILED DESCRIPTION OF THE PREFERRED EMBODIMENTS

Figure 1:
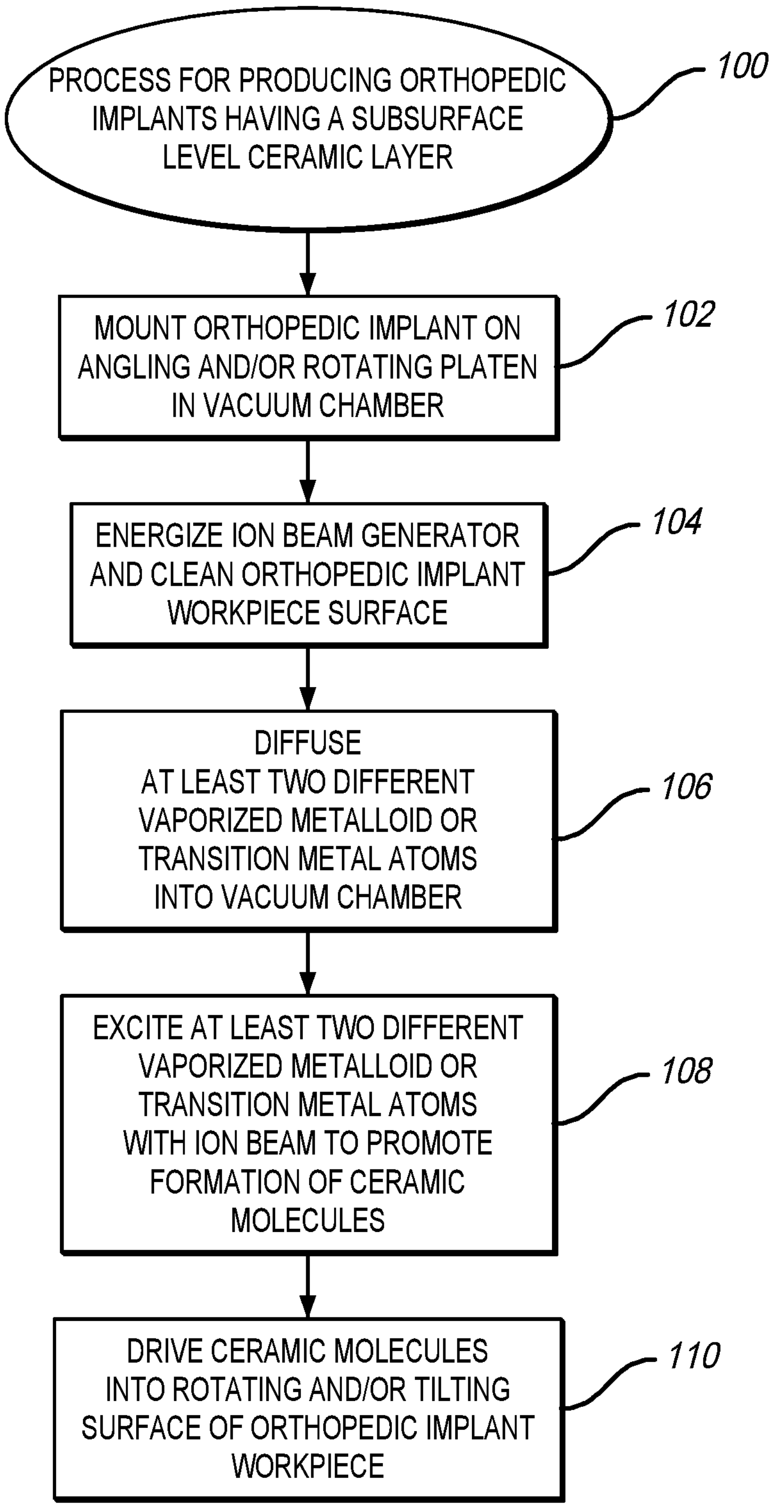
FIG. 1 is a flowchart illustrating a process for producing orthopedic implants having a subsurface level ceramic bombardment layer, as disclosed herein.
Figure 4A:
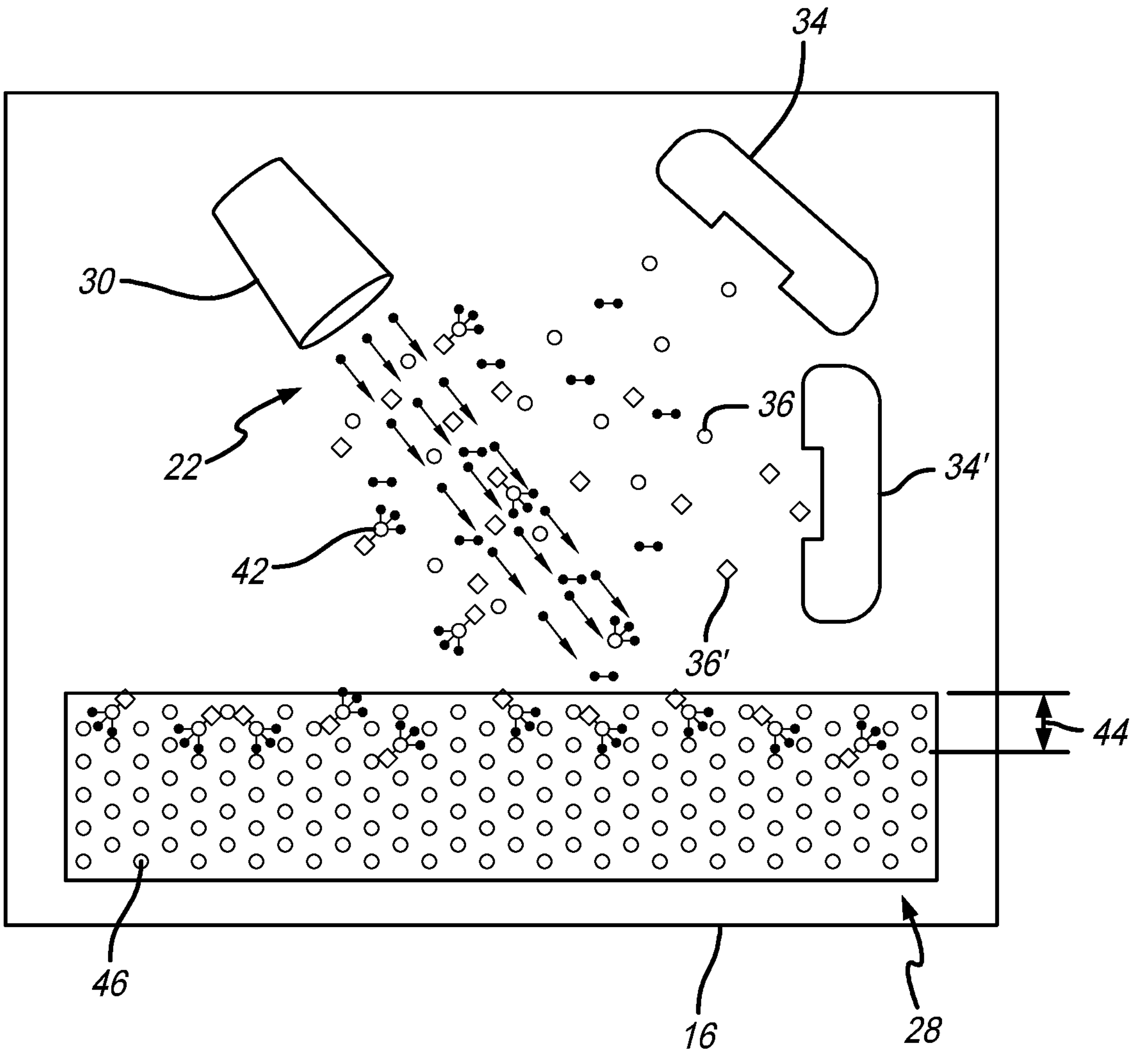
FIG. 4*a* is a diagrammatic view illustrating the ion beam driving the ceramic molecules into the angling and/or rotating surface of the orthopedic implant, thereby forming a subsurface intermixed layer.
Figure 4B:
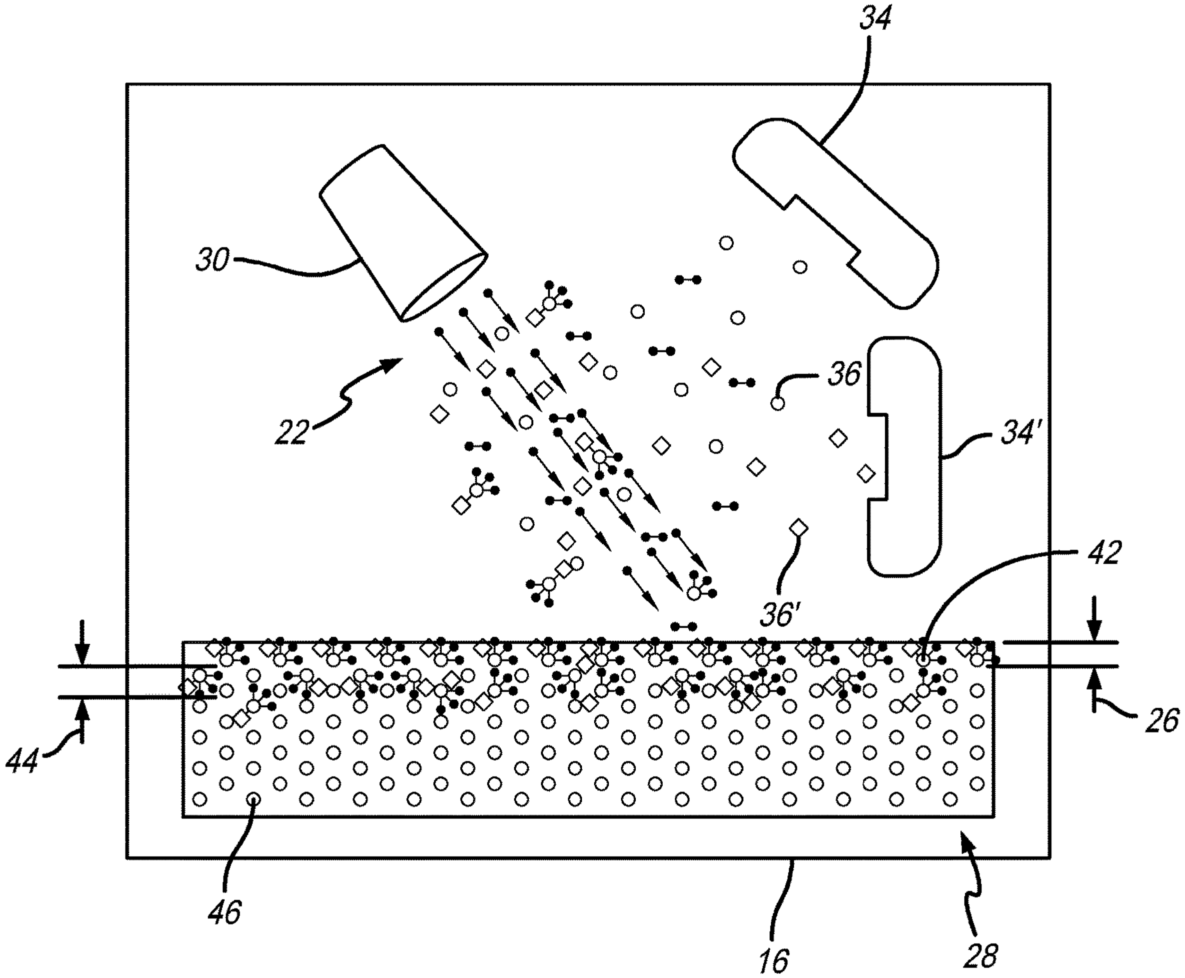
FIG. 4*b* is a diagrammatic view illustrating the ion beam further driving the ceramic molecules into the angling and/or rotating surface of the orthopedic implant, thereby forming a subsurface ceramic layer of relatively uniform thickness over the subsurface intermixed layer.
Figure 5:
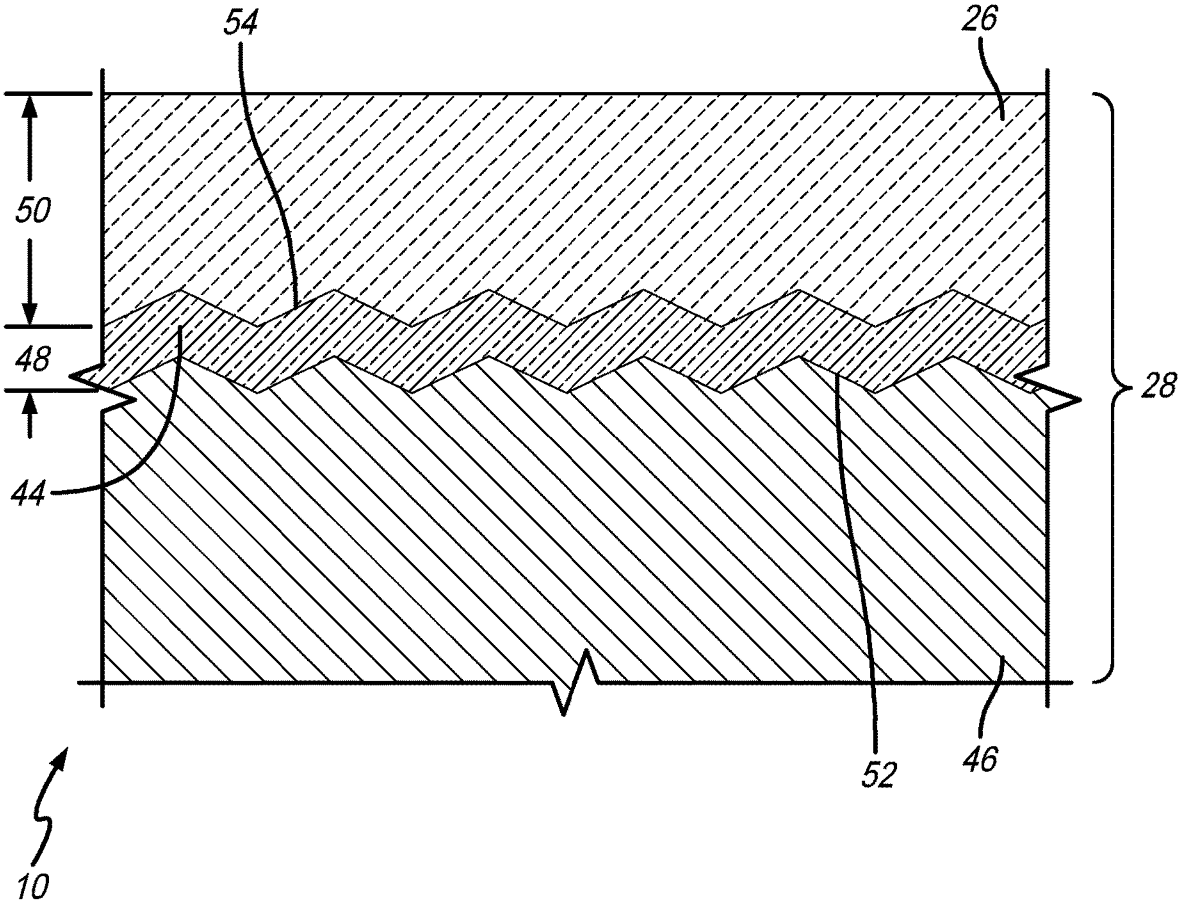
FIG. 5 is a cross-sectional view of the orthopedic implant having the subsurface ceramic layer produced by the ion beam implantation or bombardment of the ceramic molecules therein.

As shown in the exemplary drawings for purposes of illustration, the processes for producing orthopedic implants having a subsurface level ceramic bombardment layer is referred to by numeral (100) with respect to the flowchart in FIG. 1, while FIGS. 2-4*b* more specifically illustrate the operation of said processes, and FIG. 5 illustrates an exemplary orthopedic implant with a subsurface level ceramic bombardment layer 10. More specifically, the first step (102) in the process (100), as shown in FIG. 1, is to mount an orthopedic implant workpiece 12 onto an angling and/or rotating part platen 14 inside a vacuum chamber 16 suitable for performing ion beam implantation (e.g., ion beam enhanced deposition (IBED)). The processes disclosed herein improve the integration of a ceramic into the orthopedic implant by kinetically driving ceramic molecules into a subsurface layer of the orthopedic implant. This improved integration of the ceramic reduces delamination and prevents future wear and corrosion. Furthermore, the processes disclosed herein can reduce energy costs by performing the IBED process at temperatures well below 200 degrees Celsius and without a heat treatment step. Accordingly, the processes disclosed herein also reduce energy costs associated with manufacturing the related implant products.

Figure 2:
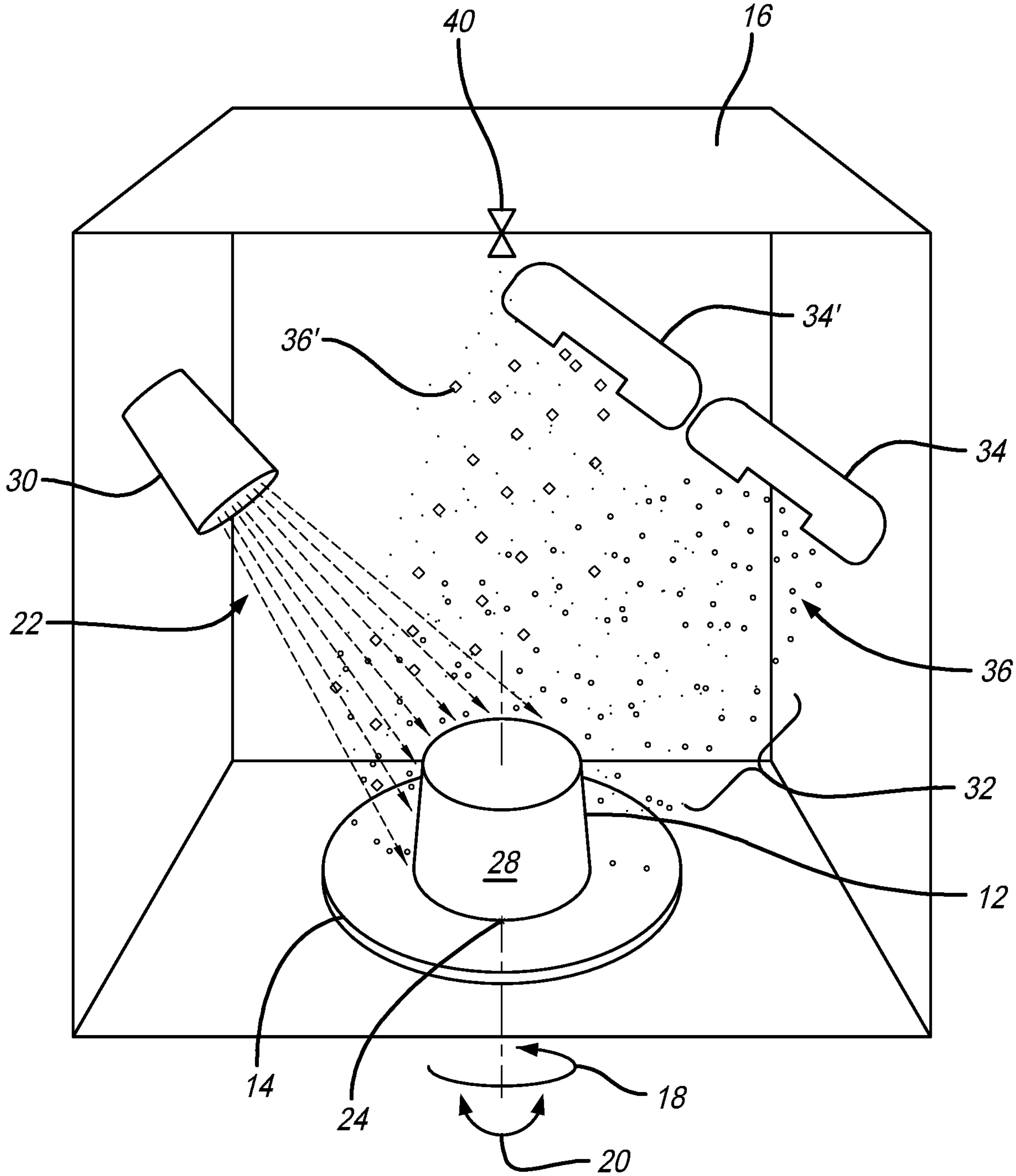
FIG. 2 is a diagrammatic view of an ion beam enhanced deposition (IBED) chamber, in accordance with the embodiments disclosed herein.

More specifically, FIG. 2 illustrates the orthopedic implant workpiece 12 mounted to the angling and/or rotating part platen 14 within the vacuum chamber 16. The orthopedic implant workpiece 10 may be made from a variety of metal alloys known in the art, such as cobalt, titanium, zirconium alloy, etc. In other embodiments, the orthopedic implant workpiece 10 may be made from ceramic materials known in the art, such as alumina ($Al_2O_3$) or zirconia ($ZrO_2$). In still other embodiments, the orthopedic implant workpiece 10 may be made from organic polymers or composites of organic polymers. Of course, persons of ordinary skill in the art may recognize that the processes disclosed herein may be used with other types of materials, and that the scope of the present disclosure should not be limited only to those materials mentioned above. The part platen 14 may be able to rotate about a center axis 18 and/or tilt about a vertical axis 20 to facilitate maximum exposure of the orthopedic implant workpiece 10 to an ion beam 22 during the ceramic implantation process. In one embodiment, the orthopedic implant workpiece 10 may couple to the part platen 14 via an attachment 24 that may include a grip, clamp, or other device having a high friction surface to retain (e.g., by compression fit) the orthopedic implant workpiece 10. In this respect, any attachment known in the art capable of sufficiently securing the orthopedic implant workpiece 10 to the part platen 14, as the part platen 14 rotates and/or tilts, will suffice. The vacuum chamber 16 maintains a high vacuum environment during the ceramic implantation process to promote the propagation of ions from the ion beam 22 toward the surfaces of the orthopedic implant workpiece 10. The high vacuum environment additionally reduces the amount of contaminant gases present to prevent contamination of a ceramic layer 26 (shown best in FIG. 5) subsequently bombarded or implanted into a surface 28 of the orthopedic implant workpiece 10. In further embodiments, a plurality of the part platens 12 may be present within the vacuum chamber 16 during the ceramic implantation process. In this embodiment, a plurality of the orthopedic implant workpieces 10 may be mounted in an array on each of the part platens 12 to produce multiple ceramic-implanted orthopedic implants 10 during each ceramic implantation process.

Once the orthopedic implant workpiece 10 has been mounted on the part platen 14, the next step (104), as shown in FIG. 1, is to energize an ion beam generator 30 to produce the ion beam 22 of energized nitrogen ions capable of penetrating into the surface 28 of the orthopedic implant workpiece 10 as it rotates about the center axis 18 and/or pivots about the vertical axis 20. Here, FIG. 2 illustrates the ion beam generator 30 emitting the ion beam 22 directed at the surface 28 of the orthopedic implant workpiece 10. In one example, the ion beam generator 30 can include a Kaufman ion source (e.g., a gridded broad beam ion source of permanent magnet design). The ion beam generator 30 can be capable of delivering nitrogen ions (e.g., N+ ions and/or $N_2$+ ions) at beam energies up to 102 kiloelectron volts (KeV) at currents up to 6 mA. In one embodiment, the beam energy may be in the range of 0.1 to 100 KeV; and in another embodiment, the beam energy may be in the range of 0.1 to 20 KeV. The ion beam 22 initially bombards the surface 28 of the orthopedic implant workpiece 10 with energized nitrogen ions during an ion beam cleaning process, thereby cleaning and augmenting the surface 28 of the orthopedic implant workpiece 10. Specifically, the initial bombardment of the orthopedic implant workpiece 10 during step (104) efficiently removes absorbed water vapor, hydrocarbons, and other substrate surface contaminants from the surface 28 of orthopedic implant workpiece 10. Removal of the substrate surface contaminants results in better implantation when the ceramic layer 26 is subsequently added to the subsurface of the orthopedic implant workpiece 10. Step (104) may also create defects in the surface 28 of orthopedic implant workpiece 10 which further promotes the subsequent implantation of the ceramic layer 26. At step (104) of the ceramic implantation process, relatively low energy ions (e.g., at beam energies between 1-1000 eV) can be employed to minimize sputtering at the surface 28 of orthopedic implant workpiece 10, while still being sufficiently energetic to produce the desired effects mentioned above.

Once the surface 28 of the orthopedic implant workpiece 10 has been cleaned and augmented by the ion beam 22, the next step (106) in accordance with FIG. 1 is to diffuse a mixture 32 of at least two different vaporized metalloid or transition metal atoms into the vacuum chamber 16. In one embodiment, the metalloid and/or transition metal atoms vaporized into the vacuum chamber 16 may be silicon (Si), titanium (Ti), silver (Ag), gold (Au), niobium (Nb), chromium (Cr), or Molybdenum (Mo), or any combination thereof. Although, of course, any metalloid and/or transition metal atoms may be compatible with the processes disclosed herein. In this respect, a silicon, titanium, silver, gold, niobium, chromium, and/or molybdenum ingot can be used as source materials to produce the mixture 32. In this regard, as shown in FIG. 2, a first evaporator 34 located within the vacuum chamber 16 may produce a quantity of a first vaporized metalloid or transition metal atom 36 by electron beam evaporation, and a second evaporator 34' may produce a quantity of a second vaporized metalloid or transition metal atom 36' by electron beam evaporation. Here, the evaporators 34, 34' may direct an electron beam (not shown) at a silicon, titanium, silver, gold, niobium, chromium, and/or molybdenum ingot workpiece (also not shown) to provide a direct flux of the vaporized metalloid or transition metal atoms 36, 36', which disperse within the vacuum chamber 16 as shown. In alternative embodiments, a single evaporator 34 may be used to produce the at least two different vaporized metalloid or transition metal elements 36, 36'. The ion beam 22 may then energize the mixture 32 to form ceramic molecules 42, as discussed in detail herein.

Once the mixture 32 has been introduced into the vacuum chamber 16, the next step (108) as shown in FIG. 1 is to promote and control the reaction of the at least two different vaporized metalloid or transition metal atoms 36, 36' in the mixture 32 using the ion beam 22, as shown in FIGS. 3*a*-3*b*. First, the positively charged nitrogen ions of the ion beam 22 collide with and kinetically excite the at least two different vaporized metalloid or transition metal atoms 36, 36' to promote the reaction process generally shown in FIG. 3*a*. Once kinetically excited, the vaporized metalloid or transition metal atoms 36, 36' react to form the ceramic molecules 42 as shown in FIG. 3*b*. The ceramic molecules 42 may be non-oxide nitride ceramic molecules and, e.g., may include SiNAg, SiAuN, SiNbN, SiCrN, SiMoN, TiSiN, TiNAg, TiNAu, TiNbN, TiCrN, TiMoN, AgAuN, NbNAg, CrNAg, MoNAg, AuNbN, AuCrN, AuMoN, NbCrN, NbMoN, CrMoN, etc. Of course, any combination of the different elements may be used so long as the ceramic molecules 42 are formed. For example, if titanium, niobium, and silver are used, the ceramic molecules 42 may be TiNbNAg. The rate of formation of the ceramic molecules 42 can be controlled by varying the energy and/or the density of the ion beam 22. For example, increasing the energy and/or density of the ion beam 22 increases the rate of formation of the ceramic molecules 42, and vice versa. As the vaporized metalloid and/or transition metal atoms 36, 36' react during step (108) to form ceramic molecules 42, a controlled backfill of vaporized metalloid and/or transition metal atoms 36, 36' may be employed to maintain the desired concentration of reactant molecules in the vacuum chamber 16.

In some embodiments of the processes disclosed herein, steps (106) and (108) may be performed without halting the cleaning process described in step (104). That is, the vaporized metalloid and/or transition metal atoms 36, 36' may be introduced into the vacuum chamber 16 without halting the ion beam cleaning process of step (104). In this way, the ion beam 22 immediately begins promoting the reaction of the vaporized metalloid and/or transition metal atoms 36, 36' once introduced into vacuum chamber 16. This can be more efficient from a manufacturing standpoint by reducing the duration required to perform the ceramic implantation process disclosed herein. Additionally, introducing the vaporized metalloid and/or transition metal atoms 36, 36' without halting the cleaning process can prevent subsequent contamination of the substrate surface 28. This may further promote generation of the subsurface ceramic layer 26 in the surface 28 of the orthopedic implant workpiece 10.

Once the ceramic molecules 42 are formed, the ion beam 22 subsequently drives the ceramic molecules 42 into the surface 28 of the rotating and/or pivoting orthopedic implant workpiece 10, per step (110) in FIG. 1. The high-energy nitrogen ions of the ion beam 22 collide with the ceramic molecules 42 to impart kinetic energy thereto. The energized ceramic molecules 42 subsequently collide with the surface 28 of the orthopedic implant workpiece 10 and bombard or implant therein, thereby initially forming a subsurface intermixed layer 44, as shown in FIG. 4*a*. The ceramic molecules 42 bombarded or implanted therein integrate with the surface 28, as opposed to simply be deposited on the surface 28 as an over surface coating, as is the current practice with known silicon nitride deposition procedures. The intermixed layer 44 is basically a transition region wherein the surface molecules 46 of the orthopedic implant workpiece 10 become intermixed with the ceramic molecules 42 as a result of the energized bombardment by way of the ion beam 22. The accumulation of ceramic molecules 42 within the intermixed layer 44 results in alloyed ceramic molecules 42 and substrate molecules 46. By varying the energy and/or density of the beam 22, persons skilled in the art can vary the depth into which the ceramic molecules 42 are driven.

As the intermixed layer 44 develops, the ion beam 22 continues to drive the ceramic molecules 42 into the subsurface of the surface 28 of the orthopedic implant workpiece 10. As shown in FIG. 4*b*, through time, the ceramic layer 26 subsequently begins to form above the intermixed layer 44. The depth the ceramic layer 26 forms into the subsurface of the surface 28 varies according to various variables, including the energy and/or density of the ion beam 22 (i.e., higher energy or greater density results in a thicker or deeper ceramic layer 26, and vice versa) and/or the duration of bombardment with the ion beam 22 (i.e., a longer bombardment in a particular area may result in a thicker or deeper ceramic layer 26, and vice versa). Similarly, varying the rate of nitrogen ion arrival can affect the stoichiometry of the resulting ceramic layer 26. For example, the nitrogen ion arrival rate may be in the range of about one (1) nitrogen ion to about five (5) nitrogen ions for each vaporized metalloid and/or transition metal atoms 36, 36' in the mixture 32. Persons of ordinary skill in the art may vary the nitrogen ion arrival rate to obtain a ceramic suitable for the desired application.

As a result of step (110), the ceramic layer 26 is molecularly integrated into the subsurface of the surface 28 (e.g., as shown in FIG. 5) of the orthopedic implant workpiece 10 and exhibits superior retention relative to silicon nitride coatings simply deposited as an over coating on the surface 28 by traditional PVD processes. This is due, at least in part, to the high strength of the alloy bond formed at an atomic level by the ion bombardment, which creates the intermixed layer 44 between the ceramic layer 26 and the surface molecules 46 of the orthopedic implant workpiece 10. As such, this ultimately changes the atomic foundation of the subsurface of the orthopedic implant workpiece 12. As the bombardment continues, the outermost ceramic layer 26 builds up, and does so over the entire orthopedic implant workpiece 12 as it rotates and/or pivots with the part platen 14. Although, of course, the processes disclosed herein may include application to only a part of the orthopedic implant workpiece 12, e.g., the articulation surfaces, as opposed to the entire orthopedic implant workpiece 12. The articulation surfaces may later be polished, along with adjacent surfaces or other fixation surfaces. The material properties of the orthopedic implant workpiece 12, in combination with the energy intensity characteristics of the ion beam 22, limit the penetration depth to attain a more consistently uniform ceramic layer 26. In this regard, the ceramic layer 26 is less likely to delaminate from the orthopedic implant workpiece 10 when compared to conventional PVD coatings. As such, the processes and implants disclosed herein are able to attain the benefits of ceramics across different types of surface finishes and surface requirements of an orthopedic implant.

During step (110), the surface 28 of the orthopedic implant workpiece 10 increases in temperature as a result of bombardment by the ion beam 22. As such, a cooler can be utilized to cool the ceramic layer 26, the intermixed layer 44, and/or orthopedic implant workpiece 10 in general to prevent adverse or unexpected changes in the material properties due to heating. In this respect, cooling may occur in and/or around the area of the orthopedic implant workpiece 10 being bombarded or implanted with the ceramic layer 26, and including the part platen 14. Water or air circulation-based coolers may be used with the processes disclosed herein to provide direct or indirect cooling of the orthopedic implant workpiece 10.

FIG. 5 is a diagrammatic cross-sectional view illustrating the surface 28 of the orthopedic implant workpiece 10, including the resultant intermixed layer 44 and the ceramic layer 26 formed into the subsurface thereof. The processes disclosed herein result in the intermixed layer 44 having a thickness 48 and the ceramic layer 26 having an implantation thickness 50, as shown in FIG. 5. The intermixed layer 44 is positioned generally between the unaffected surface molecules 46 and the ceramic layer 26. Accordingly, the intermixed layer 44 may form a uniform layer immediately above the unaffected surface molecules 46, such as designated by a boundary 52, and the ceramic layer 26 may form a uniform layer immediately above the intermixed layer 44, such as designated by a boundary 54. The intermixed width 48 and the depth of the boundary 52 may vary depending on the energy and/or density of the ion beam 22, to increase (i.e., higher energy and/or density) or decrease (i.e., lower energy and/or density) the integration or implantation of the ceramic molecules 42 into the subsurface of the surface 28 of the orthopedic implant workpiece 10. Likewise, the implantation thickness 50 and the depth of the boundary 54 may vary depending on the energy and/or density of the ion beam 22, to increase (i.e., higher energy and/or density) or decrease (i.e., lower energy and/or density) the integration or implantation of the ceramic molecules 42 into the subsurface of the surface 28 of the orthopedic implant workpiece 10. In an exemplary embodiment, the intermixed width 48 may be between 0.1-100 nanometers, while the implantation thickness 50 may be between 1-10,000 nanometers.

The resulting ceramic layer 26 may exhibit excellent tribological properties, including long-term material stability and high biocompatibility, at least relative to alumina. Likewise, the ceramics may be semitransparent to X-rays and non-magnetic, thereby allowing MRI of soft tissues proximal to ceramic coated implants. Meanwhile, the ceramics may also have wear rates comparable to alumina. Furthermore, unlike zirconia, which is a good conductor of electricity, the ceramics may advantageously have high electrical resistivity, such as on the order of $10^{16}$ Ω·cm. Ceramics, e.g., containing silver (Ag) may have anti-microbial and/or anti-colonial properties that inhibit or prevent the growth of bacteria on the implant.

Although several embodiments have been described in detail for purposes of illustration, various modifications may be made without departing from the scope and spirit of the invention. Accordingly, the invention is not to be limited, except as by the appended claims.

What is claimed is:

1. An orthopedic implant, comprising:

a base material;

an intermix transition zone molecularly integrated with the base material and comprising a mixture of the base material and a plurality of ceramic-based molecules comprising at least two different metalloid or transition metal atoms embedded into the base material underneath an original outermost surface of the base material of the orthopedic implant; and an integrated ceramic surface layer molecularly integrated with and extending from the intermix transition zone and forming at least part of a molecular structure of an outer surface of the orthopedic implant, the integrated ceramic surface layer and the base material cooperating to sandwich the intermix transition zone in between, wherein the intermix transition zone comprises a thickness of about 0.1-100 nanometers.

2. The orthopedic implant of claim 1, wherein the metalloid atoms comprise silicon atoms.

3. The orthopedic implant of claim 1, wherein the transition metal atoms comprise titanium, silver, gold, niobium, chromium, or molybdenum.

4. The orthopedic implant of claim 1, wherein the integrated ceramic surface layer comprises a relatively uniform depth.

5. The orthopedic implant of claim 4, wherein the integrated ceramic surface layer covers less than an entire surface area of the base material.

6. The orthopedic implant of claim 5, wherein the base material includes the integrated ceramic surface layer on an articulating surface only.

7. The orthopedic implant of claim 1, wherein the base material comprises a metal alloy selected from the group consisting of cobalt, titanium, and zirconium, a ceramic material selected from the group consisting of alumina ($Al_2O_3$) and zirconia ($ZrO_2$), an organic polymer, or a composite organic polymer.

8. The orthopedic implant of claim 1, including an alloy bond between the ceramic surface layer and the base material at an atomic level by ion bombardment.

9. The orthopedic implant of claim 1, wherein the intermix transition zone and the integrated ceramic surface layer comprise an aggregate thickness of about 1-10,000 nanometers.

10. The orthopedic implant of claim 1, wherein the orthopedic implant incorporating the integrated ceramic surface layer comprises an electrical resistivity of about $10^{16}$ Ω·cm.

11. The orthopedic implant of claim 1, wherein the orthopedic implant comprises a hip implant, a knee implant, or a shoulder implant.

12. The orthopedic implant of claim 1, wherein the integrated ceramic surface layer is selected from the group consisting of SiNAg, SiAuN, SiNbN, SiCrN, SiMON, TiSiN, TiNAg, TiNAu, TiNbN, TiCrN, TiMON, AgAuN, NbNAg, CrNAg, MoNAg AuNbN, AuCrN, AuMoN, NbCrN, NbMON, or CrMoN.

13. An orthopedic implant, comprising:

a base material;

an intermix transition zone molecularly integrated with the base material and having a thickness of about 0.1-100 nanometers and comprising a mixture of the base material and a plurality of ceramic-based molecules comprising at least two different metalloid or transition metal atoms embedded into the base material underneath an original outermost surface of the base material of the orthopedic implant; and an integrated ceramic surface layer molecularly integrated with and extending from the intermix transition zone and comprising a relatively uniform thickness forming at least part of the molecular structure of an articulating surface of the orthopedic implant, the integrated ceramic surface layer and the base material cooperating to sandwich the intermix transition zone in between, the intermix transition zone and the integrated ceramic surface layer comprising an aggregate thickness of about 1-10,000 nanometers.

14. The orthopedic implant of claim 13, wherein the metalloid atoms comprise silicon and the transition metal atoms comprise one of titanium, silver, gold, niobium, chromium, or molybdenum.

15. The orthopedic implant of claim 13, wherein the integrated ceramic surface layer covers less than an entire surface area of the base material, and the orthopedic implant incorporating the integrated ceramic surface layer comprises an electrical resistivity of about $10^{16}$ Ω·cm.

16. The orthopedic implant of claim 13, wherein the base material comprises a metal alloy selected from the group consisting of cobalt, titanium, and zirconium, a ceramic material selected from the group consisting of alumina ($Al_2O_3$) and zirconia ($ZrO_2$), an organic polymer, or a composite organic polymer.

17. The orthopedic implant of claim 13, including an alloy bond between the ceramic surface layer and the base material at an atomic level by ion bombardment, wherein the orthopedic implant comprises a hip implant, a knee implant, or a shoulder implant.

18. The orthopedic implant of claim 13, wherein the integrated ceramic surface layer is selected from the group consisting of SiNAg, SiAuN, SiNbN, SiCrN, SiMON, TiSiN, TiNAg, TiNAu, TiNbN, TiCrN, TiMON, AgAuN, NbNAg, CrNAg, MoNAg AuNbN, AuCrN, AuMON, NbCrN, NbMON, or CrMoN.

* * * * *